United States Patent [19]
Paul

[11] Patent Number: 6,074,364
[45] Date of Patent: Jun. 13, 2000

[54] BLOOD VESSEL CANNULATION DEVICE

[76] Inventor: Kamaljit Singh Paul, 3220 Old Orchard La., Oshkosh, Wis. 54901

[21] Appl. No.: 08/889,652

[22] Filed: Jul. 8, 1997

Related U.S. Application Data

[63] Continuation-in-part of application No. 08/634,564, Apr. 18, 1996, Pat. No. 5,733,262.

[51] Int. Cl.$^7$ ..................................................... A61M 5/00
[52] U.S. Cl. .......................... 604/116; 604/174; 604/715; 128/DIG. 26
[58] Field of Search ................................... 604/174, 179, 604/180, 116; 128/DIG. 26

[56] References Cited

U.S. PATENT DOCUMENTS

| | | | |
|---|---|---|---|
| 2,402,306 | 6/1946 | Turkel | 128/215 |
| 3,210,816 | 10/1965 | Clemons | 24/73 |
| 4,212,297 | 7/1980 | Johnson, Jr. et al. | 128/207.14 |
| 4,883,053 | 11/1989 | Simon | 128/303 B |
| 4,898,178 | 2/1990 | Wedel | 128/662.05 |
| 4,955,864 | 9/1990 | Hajduch | 604/174 |
| 5,167,630 | 12/1992 | Paul | 604/179 |

*Primary Examiner*—Wynn Wood Coggins
*Assistant Examiner*—N. Kent Gring
*Attorney, Agent, or Firm*—Thomas D. Wilhelm

[57] ABSTRACT

This invention pertains to blood vessel cannulation devices and methods for sensing the location of a blood vessel. The blood vessel cannulation device preferably comprises a mounting assembly for securing the device to a patient in the vicinity of a blood vessel, a rotating assembly mounted to the mounting assembly, and a guide housing mounted to the rotating assembly. Sensing guides in the guide housing receive one or more sensors which sense the blood vessel. Rotating the rotating assembly, and traversing the guide housing, enable bringing the bottom ends of the sensing guides into alignment with the blood vessel, correspondingly also bringing a cannula guide, in the guide housing, into alignment with the blood vessel. Cannulation, is improved by the alignment of the bottom end of the cannula guide with respective bottom ends of the sensing guides. Some embodiments of the invention may be employed using only the guide housing and a cannula, including placing markings at first and second spaced locations on a blood vessel, aligning first and second sensing guides of the guide housing with the first and second markings, with the guide housing on the blood vessel of the patient, placing a cannula proximate the blood vessel of the patient at a cannula guide in the guide housing, and inserting the cannula into the blood vessel.

28 Claims, 4 Drawing Sheets

BLOOD VESSEL CANNULATION DEVICE

This application is a continuation-in-part of U.S. patent application Ser. No. 08/634,564, filed Apr. 18, 1996, now U.S. Pat. No. 5,733,262.

FIELD OF THE INVENTION

This invention relates to devices and methods for sensing the location of a blood vessel.

BACKGROUND OF THE INVENTION

This invention pertains specifically to locating a blood vessel of a patient for cannulation, and guiding a cannula for subsequent insertion into the blood vessel, for purposes of adding substances (e.g. medicine), removing substances (e.g. blood samples), monitoring the patient (e.g. blood pressure), or the like.

The procedure of positively locating a blood vessel for venipuncture is difficult under certain conditions, including where the patient is in hypotension, where the blood vessel is not close to the skin due to patient obesity or other factors, where the blood vessel tends to displace during cannulation due to factors such as thickening of the wall of the blood vessel, or the like.

When locating a blood vessel for cannulation, it is desirable to accurately sense the location of the blood vessel through noninvasive means. Due to normal curvature along the length of the blood vessel, it may be difficult to accurately place a cannula if only one point on the blood vessel is located. It is thus desirable to locate the blood vessel, account for orientation of the blood vessel, and insert the cannula adjacent the location point or points to reduce the possibility of missing the blood vessel.

Once the blood vessel has been located, the cannula must be aligned along the length of the blood vessel at an angle suitable for insertion into the blood vessel, and in an imaginary plane generally passing through the blood vessel. If the angle is too great, the cannula may penetrate entirely through the blood vessel, including through the far wall of the blood vessel. If the angle with the blood vessel is too small, penetration may be difficult, or may fail. If the length of the cannula is outside the recited imaginary plane, the cannula may pass sideways out of the blood vessel whereby suitable cannulation is also frustrated.

It is an object of this invention to provide a blood vessel cannulation device which enables effectively sensing a blood vessel at a first location, and correspondingly enables effectively inserting a cannula adjacent the first location, in alignment along the blood vessel, and thus into the blood vessel.

It is another object of this invention to provide a blood vessel cannulation device which enables sensing the blood vessel, accounts for the orientation of the blood vessel by aligning the sensor location point or points with the blood vessel, and facilitates effective insertion of a cannula into the blood vessel at a suitable angle adjacent the sensed location.

It is a further object of this invention to provide a blood vessel cannulation device which enables sensing the location of a blood vessel through the use of multiple sensors with distinguishable outputs to allow for rapid and accurate location of the blood vessel, and accurate alignment of the sensors and cannula with the blood vessel.

SUMMARY OF THE DISCLOSURE

The invention is generally directed to blood vessel cannulation devices which assist in locating the blood vessel of a patient for cannulation, and which facilitate proper alignment of the canula over the blood vessel for precise and effective insertion of the cannula. Preferred blood vessel cannulation devices of the invention account for normal blood vessel orientation, and curvature, while guiding insertion of the cannula at a suitable angle, thereby increasing the probability of effective insertion of the cannula.

In preferred embodiments, a blood vessel cannulation device includes a mounting assembly for mounting the cannulation device proximate the skin of the patient in the vicinity of a blood vessel. The mounting assembly has a bottom. A rotating assembly is mounted for rotation with respect to the mounting assembly, on an axis transverse to the bottom of the mounting assembly. A guide housing is mounted for rotation with the rotating assembly, and for traverse across the rotating assembly. A first sensing guide extends through the guide housing, for inserting a sensor through the guide housing to a first end of the first sensing guide. A second cannula guide extends through the guide housing, for inserting a cannula through the guide housing to a second end of the second cannula guide. An optional third sensing guide extends through the guide housing, for inserting a sensor through the guide housing to a third end of the third sensing guide. The third end is aligned with the first and second ends.

Such a cannulation device is effective for locating a blood vessel for cannulation by rotating the rotating assembly such that the first and second ends define a line aligned with the blood vessel, and traversing the guide housing across the rotating assembly, with a sensor in the first sensing guide, until the sensor senses the blood vessel.

In general, the end of the cannula guide is aligned with the ends of the sensing guides. Preferably, the end of the cannula guide is between the ends of the sensing guides.

Preferably the sensing guides and the cannula guide are oriented at angles not perpendicular, and thus normal with respect to the bottom of the mounting assembly.

A locating assembly can be mounted to the mounting assembly, and extend downwardly from the bottom of the mounting assembly, and thereby assist in locating the mounting assembly on the skin of the patient proximate the blood vessel.

The device may include a first, and optionally a second, sensor, in the respective sensing guides, for sensing a blood vessel. Preferred sensors are ultrasonic probes.

Where two sensors are used, the outputs from the two sensors are preferably processed electronically such that the output signal from the first sensor is distinguishable from the output signal from the second sensor. The outputs may, for example be processed to provide audible outputs, having first and second pitches audibly distinguishable from each other by the human ear. Similarly, the outputs may be processed to provide visual outputs, having third and fourth outputs visually distinguishable from each other.

One method of cannulating a blood vessel of a patient includes marking the blood vessel at first and second spaced locations thereon, aligning first and second sensing guides of a guide housing with the first and second markings at the spaced locations, placing the guide housing on the blood vessel of the patient with the sensing guides so aligned over the markings, placing a cannula proximate the blood vessel of the patient at a third location in the guide housing, aligned with the sensing guides, and inserting the cannula into the blood vessel through the third location in the guide housing. Such a method utilizes only the guide housing, a marking device, and a cannula for cannulating the blood vessel.

Figure 1:
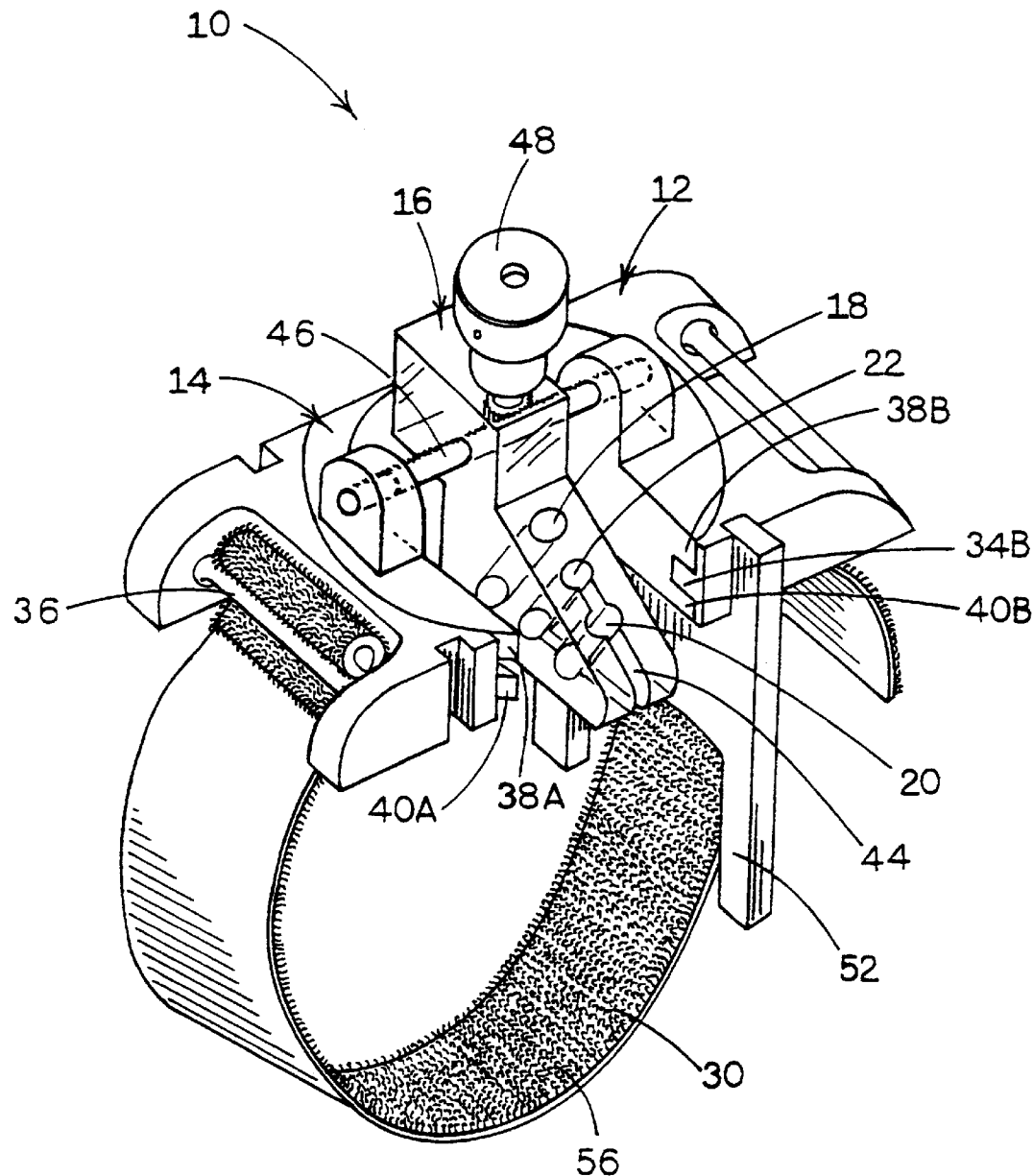
FIG. 1 shows a pictorial view of a blood vessel cannulation device of the invention.
Figure 2:
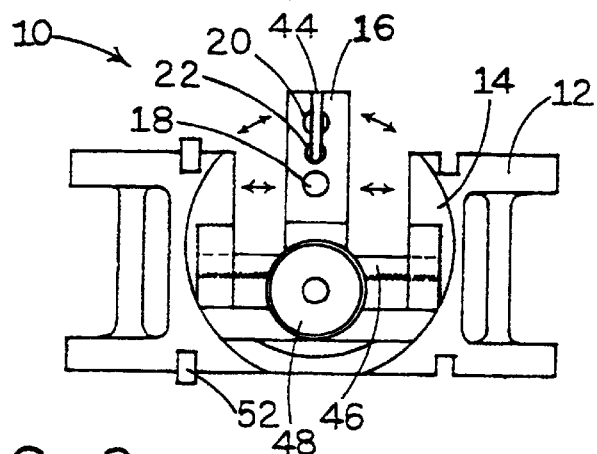
FIG. 2 shows a top view of the blood vessel cannulation device of FIG. 1.
Figure 3:
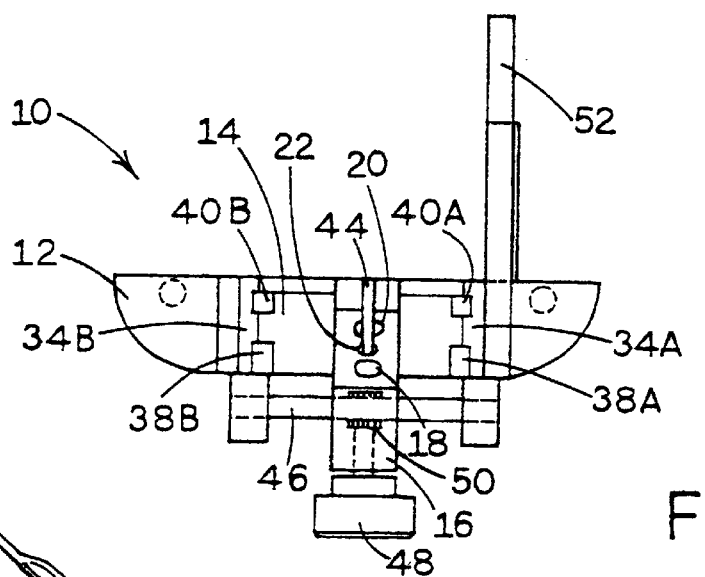
FIG. 3 shows a front view of the blood vessel cannulation device of FIG. 1 with the locating assembly mounted on the opposite side from that shown in FIG. 1.

It is to be understood that the invention is not limited in its application to the details of construction and the arrangement of the components set forth in the following description or illustrated in the drawings. The invention is capable of other embodiments or of being practiced or carried out in various ways. Also, it is to be understood that the terminology and phraseology employed herein is for purpose of description and illustration and should not be regarded as limiting. Like reference numerals are used to indicate like components.

DETAILED DESCRIPTION OF THE ILLUSTRATED EMBODIMENTS

Figure 4:
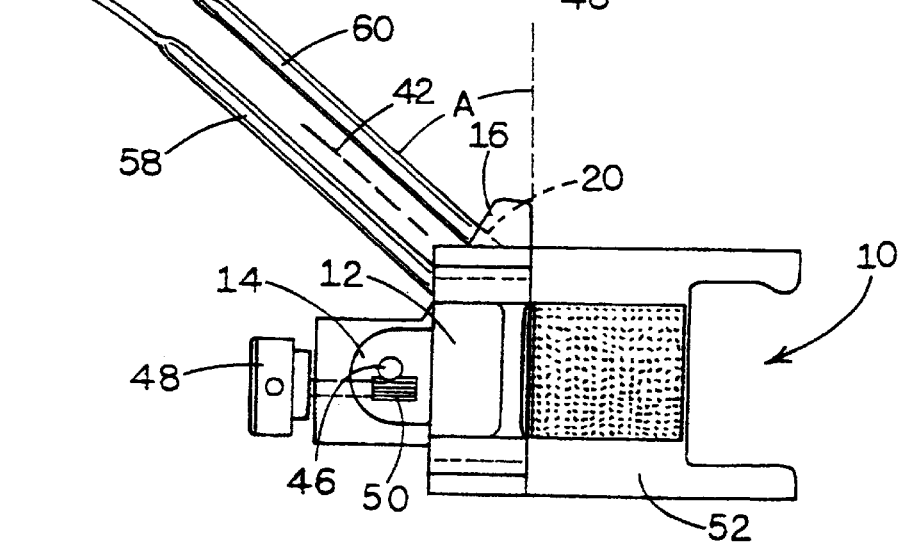
FIG. 4 shows a side view of the blood vessel cannulation device of FIG. 3, including first and second sensor probes.
Figure 5:
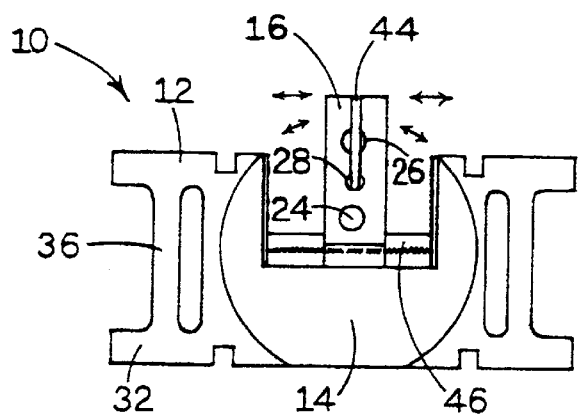
FIG. 5 shows a bottom view of the blood vessel cannulation device of FIG. 1, without the locating assembly.

Referring now by characters of reference to the drawings, and first to FIGS. 1 through 5, a blood vessel cannulation device 10 of the invention is shown. The blood vessel cannulation device comprises a mounting assembly 12. A rotating assembly 14 is mounted to the mounting assembly 12 for rotation in the directions shown by the arrows adjacent the perimeter of the rotating assembly in FIGS. 2 and 5. A guide housing 16 is mounted on, and rotates with, rotating assembly 14, and is mounted for traverse across rotating assembly 14 in the directions shown by the interiorly-disposed straight and aligned arrows in FIG. 2. Similar straight and aligned arrows are shown in FIG. 5.

Guide housing 16 includes sensing guides 18 and 20 and a cannula guide 22, all extending entirely through the guide housing 16 from a top surface of the guide housing to the bottom surface of the guide housing. The bottom end 28 (FIG. 5) of the cannula guide is aligned with the bottom ends 24 and 26 of the respective sensing guides 18 and 20. Preferably, the cannula guide 22 is oriented at a non-perpendicular angle with respect to the bottom surface 32 of the mounting assembly 12 for efficient insertion of the cannula into the blood vessel.

A strap 30 is used to mount cannulation device 10 to a patient (e.g. on a wrist) thus to place bottom surface 32 of the mounting assembly 12 securely on the skin of the patient proximate a blood vessel. In general, a first end of the strap is releasably mounted to mounting assembly 12 by an interference fit of a folded over portion 33 of the end of the strap between (i) the main body of mounting assembly 12 and (ii) a respective mounting rod 36. A rigid supporting stud, not shown, can, if desired, be mounted inside the folded over portion 33, to expand the thickness of the folded over portion for ensuring the interference fit.

Addressing a more detailed description of certain ones of the elements, and still referring to FIGS. 1 through 5, mounting assembly 12 includes a ridge 34, indicated as 34A and 34B on its opposing ends. Ridge 34 extends, optionally intermittently, about that portion of the inner perimeter of the mounting assembly which interfaces with the rotating assembly. Ridges 38, 40 extend, optionally intermittently, about that exterior portion of the rotating assembly which interfaces with the mounting assembly. Ridge 34 on mounting assembly 12 interfaces with ridges 38 and 40 on rotating assembly 14, ridges 38 and 40 being indicated as 38A and 40A adjacent end 34A, and as 38B and 40B adjacent end 34B. The respective interfacing ridges 34, 38, and 40 mount rotating assembly 14 to mounting assembly 12 while allowing for rotation of rotating assembly 14 with respect to mounting assembly 12.

Guide housing 16 includes a slot 44. Slot 44 extends inwardly from a distal edge of the guide housing, and communicates with cannula guide 22 and sensing guide 20. In some embodiments, it is contemplated that slot 44 also extends inwardly to, and communicates with, sensing guide 18. As illustrated in the drawings, slot 44 preferably extends through the entire height of the guide housing, from the top of the guide housing to the bottom thereof. Slot 44 facilitates removal of the cannulation device 10 from the patient after a cannula has been inserted into the blood vessel, and while the cannula remains so inserted.

Other constructions of the guide housing are contemplated, including a multi-piece guide housing which can be disassembled, to facilitate removal of cannulation device 10 from the patient after the cannula has been inserted into the blood vessel. An example of such multi-piece guide housing is shown in my U.S. Pat. No. 5,167,630, herein incorporated by reference in its entirety.

Rotating assembly 14 includes a rail 46 extending thereacross. A dial gear 50, attached to a positioning dial 48 on guide housing 14, interfaces with rail 46. Teeth on dial gear 50 cooperate with corresponding teeth on rail 46. Rotation of dial 48 causes corresponding rotation of dial gear 50 which causes guide housing 16 to traverse transversely back and forth along rail 46, across the rotating assembly 14, the direction of traverse depending on the direction in which dial 48 is turned.

Figure 6A:
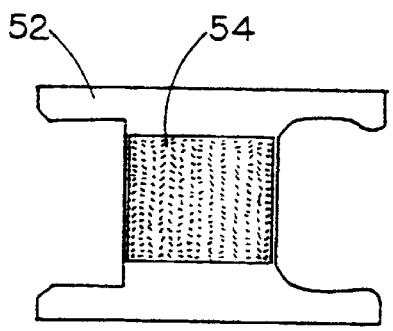
FIG. 6A shows a top view of the locating assembly.
Figure 6B:
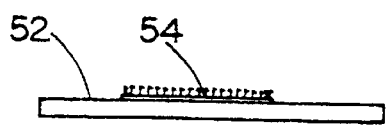
FIG. 6B shows a side view of the locating assembly.
Figure 7:
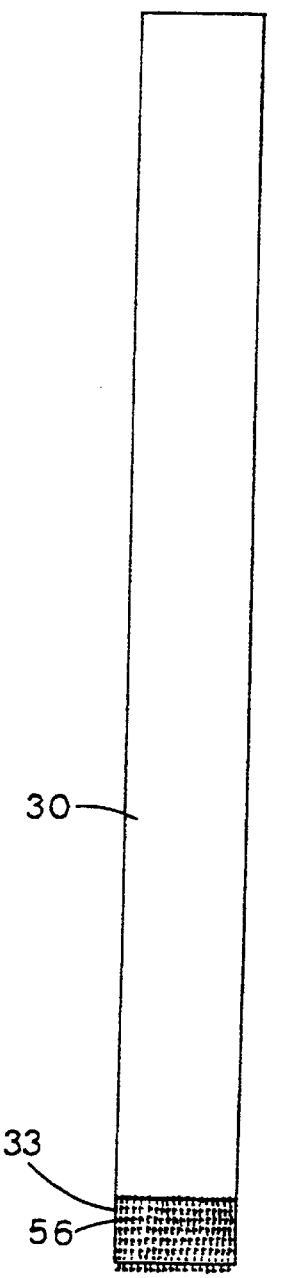
FIG. 7 shows a mounting strap used to mount the cannulation device of FIG. 1 to a patient.

A locating assembly 52, shown individually in FIGS. 6A and 6B, is attached to mounting assembly 12 on either side thereof at respective slots shown in FIGS. 1, 2, 3, and 5, and extends downwardly with respect to bottom surface 32, as seen in FIGS. 1 through 4 to aid in locating cannulation device 10 on the patient (e.g. at the patient's wrist). A first fastener 54 on locating assembly 52 cooperates with a corresponding second fastener 56 on the mounting strap, thus releasably mounting strap 30 to the locating assembly, and thereby releasably securing cannulation device 10 to the patient. Fasteners 54 and 56 preferably have cooperating hooks and loops to provide the fastening means. Other fastening means could be used.

Cannulation device 10 is mounted to the wrist of a patient as follows. With the palm of the hand facing upwardly, and with bottom surface 32 of the mounting assembly resting on the up-turned wrist, locating assembly 52 is brought into abutment with preferably the thumb side of the wrist. The surface of the locating assembly which contacts the patient's skin is thus aligned generally normal to the skin of the patient which contacts bottom surface 32 of mounting assembly 12. With strap 30 releasably mounted to mounting assembly 12 at mounting rod 36, the strap is then placed around the wrist and secured to locating assembly 52 by fastening together cooperating (e.g. hook and loop) fasteners 541 and 56, thus temporarily, but securely mounting the cannulation device 10 to the wrist of the patient.

A sensor 58 (FIG. 4) is inserted into sensing guide 18 until the end of sensor 58 is proximate bottom end 24 of sensing guide 18, and thus proximate the skin of the patient. A preferred sensor is an ultrasonic sensor. Where the sensor is an ultrasonic sensor, and in any such embodiments of the invention, suitable communication media, such as a gel, is preferably positioned between the end of the sensor (e.g. sensor 58) and the skin of the patient, to complete the communication path between a blood vessel and the sensor, and thus to facilitate sensing the blood vessel. The output of the sensor is useful for sensing the location of a blood vessel to be cannulated. Positioning dial 48 is turned, causing guide housing 16 to traverse across rotating assembly 14.

As guide housing 16 traverses across rotating assembly 14, the end of sensor 58 respectively traverses across the surface of the skin at the wrist of the patient. When the end of the sensor is positioned over a pulsating blood vessel such as an artery, the change in rate of blood flow at each pulsation causes an output, from a preferred sensor, which varies with each pulsation. Thus, the variation in output from the sensor is an indication that the sensor is positioned over the blood vessel.

With the rotating member held in place stationary, sensor 58 is then removed from the first sensing guide 18 and is similarly inserted into the second sensing guide 20 until the end of sensor 58 is proximate bottom end 26 of sensing guide 20, and thus proximate the skin of the patient. Rotating assembly 14 is then rotated with respect to mounting assembly 12, and traversed across the mounting assembly, until the blood vessel is again sensed, while generally retaining the earlier location of end 24 of the first sensing guide. Sensor 58 is then removed from sensing guide 20 and alternately reinserted into sensing guides 18 and 20, making small adjustments to the lateral position of the guide housing 16, and the rotational position of rotating assembly 14, as necessary, until the blood vessel can be sensed by sensor 58 in both of sensing guides 18 and 20 without moving guide housing 16.

When the blood vessel can be sensed in both sensing guides without moving the rotating assembly or the guide housing, bottom ends 24, 26 of respective sensing guides 18, 20, are at least generally aligned with the blood vessel, and are positioned over the blood vessel. Similarly, since bottom end 28 of cannula guide 22 is aligned with bottom ends 24, 26 of the sensing guides, the cannula end, too, is typically positioned over the blood vessel. With the cannula end 28 positioned over the blood vessel, a cannula is then inserted into the cannula guide 22 at an effective angles along path 42, as illustrated in FIG. 4, until the end of the cannula reaches bottom end 28 of cannula guide 22, the cannula thus being proximate the skin of the patient and aligned over the blood vessel. The cannula is then inserted into the blood vessel as desired to complete the cannulation. With the cannula inserted into the blood vessel, the function of cannulation device 10 is completed, and the cannulation device can be removed from the patient.

In removing the cannulation device, any sensor disposed in sensing guide 20 is removed first, leaving slot 44 open and empty except for the cannula in cannula guide 22. Mounting strap 30 is, released. Guide housing 16 is then removed from around the cannula, using slot 44 as the cannula exit path, but leaving the cannula substantially immobile as inserted in the blood vessel of the patient. Any sensor in sensing guide 18 is also preferably removed from the cannulation device before the cannulation device is removed from the patient.

In another embodiment, with sensor 58 in place in sensing guide 18, a second sensor 60 is inserted into sensing guide 20 until the end of the second sensor 60 is proximate end 26 of sensing guide 20, and thus proximate the skin of the patient. The process of traversing guide housing 16 and rotating assembly 14 is then completed with both sensors in place.

In this embodiment, the outputs of the respective sensors 58, 60 are preferably distinguishable from each other to allow for concurrent sensing of the blood vessel at both sensing guide ends 24, 26. For example, using two ultrasonic sensors 58, 60 concurrently, the output signals from the sensors can be processed through conventional electronic ultrasonic processing circuitry which process ultrasonic signals, to create first and second audible outputs. The two ultrasonic processors can be adjusted, for example, to output two separate and distinct pitches, audibly distinguishable from each other by the human ear.

In other embodiments, the output signals may be processed through electronic circuitry for visual presentation such as on a cathode ray tube, wherein the two output signals are presented as visible representations of the signals and are visually distinguishable from each other by the human eye.

Whatever the output medium, the two representations can be presented in separate representational output devices, or in a single such output device having two output representations, one for each sensor.

In preferred embodiments, sensor 58, or sensors 58 and 60 are ultrasonic probes. Preferably, sensing guides 18, 20 are aligned at non-perpendicular angles "A" with respect to bottom surface 32 of mounting assembly 12. See FIG. 4. In some embodiments, guides 18, 20, and 22 are parallel to each other as shown in, for example, FIG. 1. Guides 18, 20, and 22 can all be aligned with each other in a common plane as shown in, for example, FIGS. 1–3 and 5. In the alternative, they may represent two or more intersecting planes (not shown). Such alignment of the planes is not critical. What is critical is that end 28 of the cannula guide be aligned with ends 24, 26 of the sensing guides. End 28 is preferably located between ends 24 and 26, but if not, should be sufficiently close to one of ends 24, 26 that end 28 will be over the blood vessel when the sensing guides are over the blood vessel, in spite of any normal curvature of the paths of blood vessels, such as in the wrist.

Ultrasonic probes, as preferred herein, can sense the blood when the length of the probe is oriented perpendicular to the blood vessel as taught in my U.S. Pat. No. 5,167,630. However, such ultrasonic probes sense the location of the blood vessel primarily by sensing change in flow velocity of blood elements such as the red blood cells, by a general application of the Doppler effect. Thus, any degree of alignment of the probe along the direction of flow of the blood in the vessel provides a desired increase in sensitivity of the probe to the flow of the blood, as compared to having the probe oriented perpendicular to the blood vessel. Sensitivity of the probe increases with increasing angles from the perpendicular to about 45 degrees, and then gradually diminishes as the angle is further increased from the perpendicular, until the signal is entirely lost at about 80 degrees from the perpendicular. Thus, the probe can be oriented at any angle up to about 80 degrees from the perpendicular and be operable. However, the least preferred angle is a perpendicular angle because of the lesser sensitivity of ultrasonic probes at that orientation.

Correspondingly, any angle "A" (FIG. 4) of about 10 degrees up to, but less than, 90 degrees is preferred. While 90 degrees is operable, it represents a substantial reduction, or trough, from peak sensitivity of the probe, and is thus not preferred. More preferred angles "A" are angles between about 20 degrees and about 85 degrees. Still more preferred angles are between about 25 degrees and about 80 degrees. Highly desirable angles are between about 30 degrees and about 70 degrees, where the output signal from ultrasonic sensors is particularly strong.

The angle "A" can be measured on either side of the perpendicular because blood flow can be detected whether flowing toward the face of the probe (at the bottom of the probe) or away from the face of the probe. Thus, as viewed in FIG. 4, angle "A" can be directed to either side of the dashed perpendicular line, but is preferably greater than 10 degrees when measured from the perpendicular.

As used in the claims that follow, an acute angle is any angle with respect to the bottom of the mounting assembly, except a perpendicular angle. Thus, where angle "A" as illustrated could be increased to be obtuse with respect to the bottom of guide housing 16, the complementary angle defined with respect to the bottom of guide housing 16 is an acute angle. Where the claims specify acute angle, such complementary acute angles are included.

While not critical, it is preferred that angle "A" be defined within, or substantially within, an imaginary plane generally passing through the blood vessel and perpendicular to the skin of the patient. Such orientation utilizes existing skills of medical professionals wherein such orientation is preferred for orientation of the cannula.

In order to ensure that cannulation device 10 is aligned with the blood vessel, the spacing between sensing guide ends 24, 26 should be sufficiently small to avoid misalignment due to normal curvature of the blood vessel between ends 24 and 26. Preferably, the spacing between sensing guide ends 24, 26 is less than about 1 inch. More preferably, the spacing between sensing guide ends 24, 26 is about 0.5 inch or less. To provide assurance that cannula guide end 28 will align with the blood vessel when the sensors are so aligned, cannula guide end 28 is preferably adjacent at least one of the sensing guide ends 24, 26, and is preferably between guide ends 24, 26.

In some embodiments of the invention, guide housing 16 includes a single sensing guide 18, and cannula guide 22. Sensor 58 is inserted into sensing guide 18 until the end of sensor 58 is proximate end 24 of sensing guide 18, and thus proximate the skin of the patient. Guide housing 16 is then made to traverse across rotating assembly 14, by turning positioning dial 48, until the blood vessel can be sensed by sensor 58. Rotating assembly 14 is rotated with respect to mounting assembly 12 until sensing guide end 24 and cannula guide end 28 are generally aligned over the blood vessel. A cannula is then inserted into cannula guide 22 along path 42, as shown in FIG. 4, for venipuncture. In these embodiments, an especially short spacing such as 0.25 inch or less is preferred between ends 24 and 28.

In still other embodiments of the invention, guide housing 16 is mounted directly to mounting assembly 12. Rotating assembly 14 is omitted. Thus, guide housing 16 traverses across rail 46 on mounting assembly 12. Guide housing 16 includes a single sensing guide 18 with optional second sensing guide 20, oriented at an angle "A" not perpendicular to bottom surface 32 of mounting assembly 12. End 24 of sensing guide 18 is adjacent end 28 of cannula guide 22. Sensor 58 is inserted into sensing guide 18 until the end of the sensor is proximate end 24 of sensing guide 18, and thus proximate the skin of the patient. The inventor herein has discovered that orientation of the sensing guide at a non-perpendicular angle "A" measured with respect to bottom surface 32 of mounting assembly 12 increases the probability that the sensor will accurately sense the blood vessel. Guide housing 16 is made to traverse across mounting assembly 12, by turning positioning dial 48, until the blood vessel can be sensed by sensor 58. Once the blood vessel has been sensed, a cannula is inserted into cannula guide 22 along path 42, as shown in FIG. 4, for venipuncture of an artery of vein.

While this embodiment is useful for locating blood vessels generally aligned with, for example, the length of a person's arm, rotation of the guide housing with respect to the mounting assembly is not contemplated, whereby blood vessels not aligned with the appendage to which the device is mounted may not be properly located. Accordingly, the embodiments including rotating assembly 14 are preferred.

In preferred embodiments, a blood vessel to be targeted for cannulation is first selected by selecting from those blood vessels which can be seen through the skin. Then the cannulation device 10 is mounted to the appendage (e.g. wrist) over the selected blood vessel, and on the surface of the skin. After the device is mounted to the appendage, rotating assembly 14 is rotated until the applicable guides 18, 20, and 22 are visually aligned with the selected vessel. Then one or more sensors 58, 60 are inserted in the sensing guides and connected to a appropriate output device, or devices. Communication gel is used at the ends of the sensors as appropriate. Dial 48 is then rotated to bring the ends 24 and/or 26 over the blood vessel, and to enable the sensor or sensors to thus sense the blood vessel. When the blood is sensed by a sensor at one of ends 24, 26, small adjustments are made to rotating assembly 14 and dial 48 to bring both ends 24 and 26 into position over the blood vessel, whereby the blood vessel can be sensed at both ends 24 and 26 without moving either rotating assembly 14 or guide housing 16. When the blood vessel can be sensed at both ends 24 and 26 without moving either the rotating assembly or the guide housing, both ends 24 and 26 are aligned over the blood vessel. Accordingly, end 28 of the cannula guide is also positioned over the blood vessel. The cannula can then be inserted through the cannula guide with reasonable assurance that the cannula will be properly inserted into the blood vessel.

Figure 8:
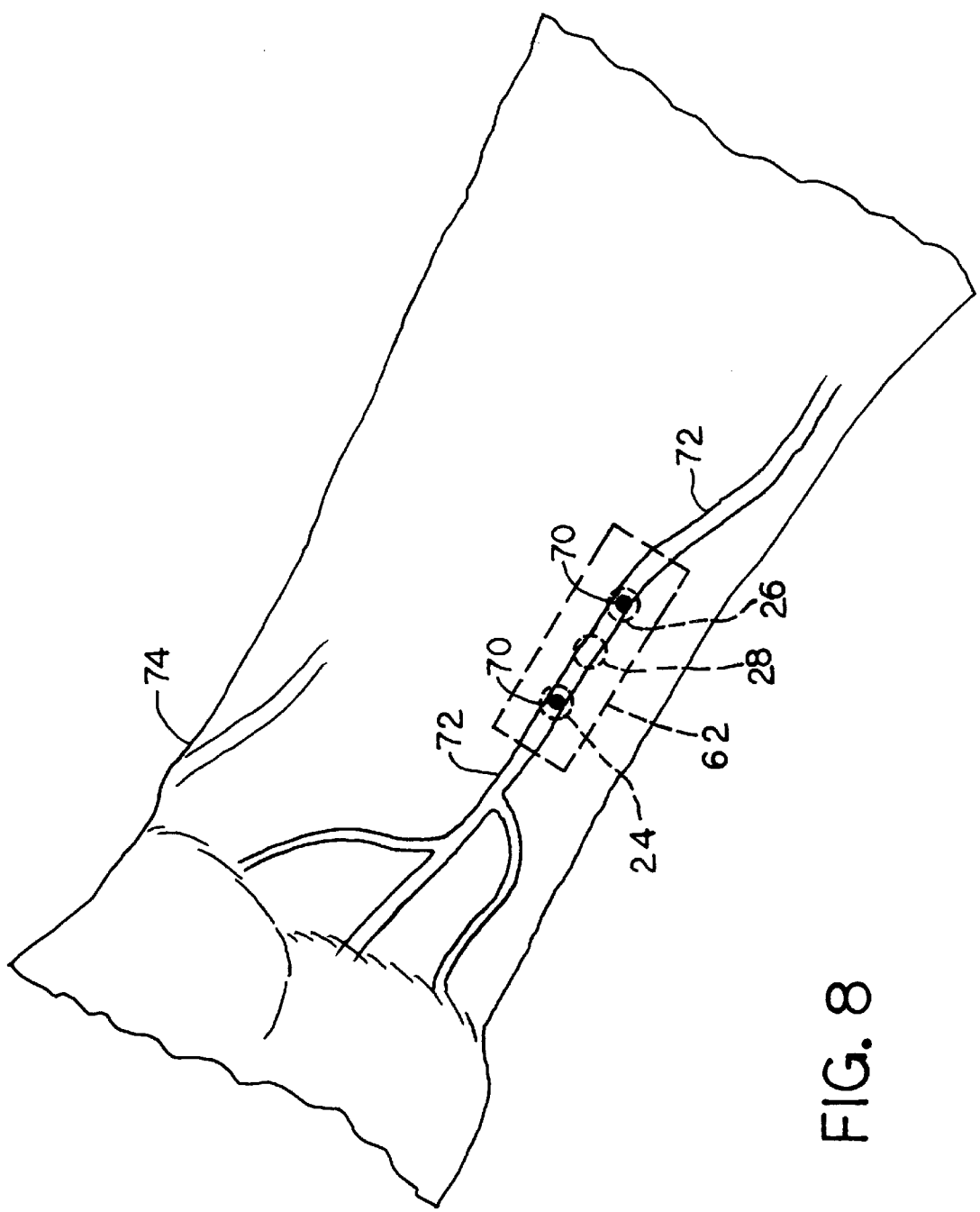
FIG. 8 shows a wrist of a patient and an imaginary projection of the bottom surface of the guide housing on the wrist.

FIG. 8 illustrates a variation on the earlier embodiments that does not utilize ultrasonic sensors and wherein only guide housing 16 need be utilized. None of the other elements shown in FIG. 1 are needed for the embodiment of FIG. 8. Only guide housing 16, a marking device, and a cannula are required. The bottom surface 64 of guide housing 16, including ends 24, 26 of sensing guides 18, 20, and end 28 of cannulation guide 22, is shown as an imaginary projection 62 in FIG. 8. Sensing guides, 18, 20 described earlier and shown in FIG. 1 act similarly as guides in this embodiment, providing visual rather than audible sensations to the medical worker.

In a method employing the embodiment of FIG. 8, marks 70 are placed at first and second spaced locations on the skin of the patient at blood vessel 72 of wrist 74 using a felt tip pen or any other suitable device which can be used to readily make a mark on the skin. Ends 24, 26 of the sensing guides of guide housing 16 are then aligned with markings 70. Guide housing 16 is placed on the skin of the patient at blood vessel 72 as shown, with sensing ends 24, 26 of sensing guides 18, 20 aligned over the respective marks 70. Gentle downward pressure is then applied on guide housing 16, thereby applying downward pressure on the skin at blood vessel 72. The downward pressure on the skin helps fix the guide housing in position on the skin by frictional engagement with the skin, and applies a respective pressure on the blood vessel such that the blood vessel may be substantially immobilized. To that effect, the downward pressure on the blood vessel urges the blood vessel inwardly of the skin, where the blood vessel is supported against further inward movement by underlying tissue such as muscle or ligaments, and is supported against transverse movement generally parallel to the skin, by adjacent tissue to the left and right of the blood vessel.

With the guide housing thus stabilized in position on the skin of the patient, a cannula is readily inserted into cannula guide 22, through the skin of the patient and into blood vessel 72 at end 28 of the cannula guide. As in the embodiments discussed earlier, slot 44 in guide housing 16 allows removal of the guide housing from around the cannula. Slot 44 in guide housing 16 is generally maintained in alignment with the cannula as guide housing 16 is physically removed from the cannula. Thus the cannula remains in blood vessel 72 and guide housing 16 no longer contacts, or is near, the skin of the patient.

In one method of making markings 70, a medical worker visually marks the blood vessel at first and second spaced locations on the skin at blood vessel 72, based on visual but otherwise unaided judgement of proper spacing of the first and second location. The medical worker thus establishes the spacing between markings 70 based on experience and skill, such that the distance between the markings approximates the distance between ends 24, 26 of the marking guides of guide housing 16.

In another method of marking the blood vessel, guide housing 16 is placed on the skin at blood vessel 72, the blood vessel is marked with a felt pen or like marking device through the sensing guides of guide housing 16. Guide housing 16 may be temporarily removed from the skin to allow the medical worker to confirm that the marks do in fact represent a blood vessel location.

The above method allows quick marking and cannulation of a patient having veins visible to the medical worker. Further, using guide housing 16, with no other elements, as a cannulation guiding device simplifies the use of the guiding apparatus, and controls the cost of such apparatus, while providing a beneficial guide for insertion of the cannula.

Guide housing 16 can have any of a variety of shapes. Guide housing 16, of course, must include cannula guide 22 and at least one of, preferably both of, sensing guides 18, 20 to act as marking guide. The height required for dial 48 and the ability to pivot shown in FIG. 1, is not required for the embodiment of FIG. 13. Thus, the shape shown in FIG. 1 is not required. For example, guides 18, 20, 22 in the embodiment of FIG. 8 can have shorter lengths than corresponding guides in the embodiment of FIG. 1.

While FIG. 8 illustrates placing the cannula into a blood vessel 72 at the wrist of a patient, the cannula may so be placed at any location on the body of the patient, having a suitable blood vessel.

Those skilled in the art will now see that certain modifications can be made to the apparatus and methods herein disclosed with respect to the illustrated embodiments, without departing from the spirit of the instant invention. And while the invention has been described above with respect to the preferred embodiments, it will be understood that the invention is adapted to numerous rearrangements, modifications, and alterations, and all such arrangements, modifications, and alterations are intended to be within the scope of the appended claims.

Having thus described the invention, what is claimed is:

1. A blood vessel cannulation device for cannulating a patient, comprising:

(a) a mounting assembly for mounting said cannulation device proximate the skin of such patient in the vicinity of a blood vessel, said mounting assembly having a bottom;

(b) a rotating assembly mounted for rotation with respect to said mounting assembly, on an axis transverse to the skin of such patient to which said cannulation device is proximate;

(c) a guide housing mounted for rotation with said rotating assembly, and for traverse across said rotating assembly;

(d) a first sensing guide extending through said guide housing, for inserting a sensor through said guide housing to a first end of said first sensing guide proximate the skin of such patient; and (f) a second cannula guide extending through said guide housing, for inserting a cannula through said guide housing to a second end of said second cannula guide proximate the skin of such patient, said cannulation device being effective for locating a blood vessel for cannulation by rotating said rotating assembly such that said first and second ends define a line aligned with the blood vessel, and traversing said guide housing across said rotating assembly until the sensor senses the blood vessel.

2. A blood vessel cannulation device as in claim 1, said second cannula guide being oriented at an acute angle with respect to said bottom of said mounting assembly.

3. A blood vessel cannulation device as in claim 1, said first sensing guide being oriented at an acute angle with respect to said bottom of said mounting assembly.

4. A blood vessel cannulation device as in claim 1, including a third sensing guide extending through said guide housing, for inserting a sensor through said guide housing to a third end of said third sensing guide proximate the skin of such patient, said third end being aligned with said first and second ends.

5. A blood vessel cannulation device as in claim 4, said third sensing guide being oriented at an acute angle with respect to said bottom of said mounting assembly.

6. A blood vessel cannulation device as in claim 4, said blood vessel cannulation device including a locating assembly extending downwardly from said bottom and assisting in locating said mounting assembly on the skin of such patient proximate the blood vessel, thereby to enable movement of said first, second, and third ends transversely across the blood vessel.

7. A blood vessel cannulation device as in claim 4, including a first sensor inserted into said first sensing guide, said first sensor providing a first output signal useful for locating the blood vessel proximate said first end, and a second sensor inserted into said third sensing guide, said second sensor providing a second output signal useful for locating the blood vessel proximate said third end.

8. A blood vessel cannulation device as in claim 7, said first and second sensors comprising ultrasonic probes.

9. A blood vessel cannulation device as in claim 7, the first output signal being distinguishable from the second output signal.

10. A blood vessel cannulation device as in claim 7, the first output signal providing an input to a first audible output device providing a third audible output signal indicating when said first end is proximate the blood vessel, the second output signal providing an input to a second audible output device providing a fourth audible output signal indicating when said third end is proximate the blood vessel, said third and fourth audible output signals having first and second pitches audibly distinguishable from each other by the human ear.

11. A blood vessel cannulation device as in claim 7, the first output signal providing an input to a first visual output device for providing a third visible output signal indicating when said first end is proximate the blood vessel, the second output signal providing an input to a second visual output device for providing a fourth visible output signal indicating when said third end is proximate the blood vessel, said third and fourth visible output signals being visually distinguishable from each other by the human eye.

12. A blood vessel cannulation device for cannulating a patient, comprising:
   (a) a mounting assembly for mounting said cannulation device proximate the skin of a patient in the vicinity of a blood vessel, said mounting assembly having a bottom;
   (b) a guide housing mounted for traverse across said mounting assembly;
   (c) a first sensing guide extending through said guide housing, for inserting a sensor through said guide housing to a first end of said first sensing guide proximate the skin of such patient, said first sensing guide being oriented at an acute angle of no more than about 85 degrees with respect to said bottom of said mounting assembly; and
   (d) a second cannula guide extending through said guide housing, for inserting a cannula through said guide housing to a second end of said second cannula guide proximate the skin of such patient,
said cannulation device being effective for locating a blood vessel for cannulation by traversing said guide housing across said mounting assembly until said sensor senses the blood vessel, thus aligning said first and second ends over the blood vessel.

13. A blood vessel cannulation device as in claim 12, said blood vessel cannulation device including a locating assembly extending downwardly from said bottom of said mounting assembly, and assisting in locating said mounting assembly on the skin of such patient proximate the blood vessel, thereby to enable movement of said first and second ends transversely across the blood vessel.

14. A blood vessel cannulating device as in claim 12, said first sensing guide being oriented at an angle of about 20 degrees to about 70 degrees with respect to said bottom of said mounting assembly.

15. A blood vessel cannulation device for cannulating a patient, comprising:
   (a) a guide housing;
   (b) a first sensing guide extending through said guide housing, for inserting a sensor through said guide housing to a first end of said first sensing guide proximate the skin of such patient;
   (c) a second sensing guide extending through said guide housing, for inserting a sensor through said guide housing to a second end of said second sensing guide proximate the skin of such patient; and
   (d) a third cannula guide extending through said guide housing, for inserting a cannula through said guide housing to a third end of said third cannula guide proximate the skin of such patient, and aligned with said first and second ends.

16. A blood vessel cannulation device as in claim 15, said cannulation device being effective for locating a blood vessel for cannulation by positioning said cannulation device proximate the skin of such patient such that the blood vessel is detectible by sensors located at both said first and second ends, the combination of said first and second sensing guides and said cannula guide thus being aligned with each other and being positioned over the blood vessel.

17. A blood vessel cannulation device as in claim 15, said first and second sensing guides being oriented at acute angles with respect to the skin of such patient, when said blood vessel cannulation device is positioned on the skin of such patient for cannulation.

18. A blood vessel cannulation device as in claim 15, said third cannula guide being oriented at an acute angle with respect to the skin of such patient, when said blood vessel cannulation device is positioned on the skin of such patient for cannulation.

19. A blood vessel cannulation device as in claim 15, including a first sensor inserted into said first sensing guide, said first sensor providing a first output signal useful for locating the blood vessel proximate said first end and a second sensor inserted into said second sensing guide, said second sensor providing a second output signal useful for locating the blood vessel proximate the second end.

20. A blood vessel cannulation device as in claim 19, the first output signal being distinguishable from the second output signal.

21. A blood vessel cannulation device as in claim 19, the first output signal providing an input to a first audible output device providing a third audible output signal indicating when said first end is proximate the blood vessel, the second output signal providing an input to a second audible output device providing a fourth audible output signal indicating when said second end is proximate the blood vessel, said third and fourth audible output signals having first and second pitches audibly distinguishable from each other by the human ear.

22. A blood vessel cannulation device as in claim 15, the first output signal providing an input to a first visual output device providing a third visible output signal indicating when said first end is proximate the blood vessel, the second output signal providing an input to a second visual output device providing a fourth visible output signal indicating when said second end is proximate the blood vessel, said third and fourth visible output signals being visually distinguishable from each other by the human eye.

23. A blood vessel cannulation device for cannulating a patient, comprising:
   (a) a mounting assembly for mounting said cannulation device proximate the skin of such patient in the vicinity of a blood vessel, said mounting assembly having a bottom;
   (b) a rotating assembly mounted for rotation with respect to said mounting assembly, on an axis transverse to said bottom of said mounting assembly;
   (c) a guide housing mounted for rotation with said rotating assembly, and for traverse across said rotating assembly;
   (d) a first sensing guide extending through said guide housing, for inserting a sensor through said guide housing to a first end of said first sensing guide;
   (f) a second cannula guide extending through said guide housing, for inserting a cannula through said guide housing to a second end of said second cannula guide; and (g) a third sensing guide extending through said guide housing, for inserting a sensor through said guide housing to a third end of said third sensing guide, said third end being aligned with said first and second ends.

24. A method of cannulating a blood vessel of a patient, the method comprising the steps of:
 (a) placing a guide housing on the skin of such patient in the vicinity of a blood vessel;
 (b) aligning the guide housing along the length of the blood vessel using first and second spaced sensor guides in the guide housing, the first and second sensor guides being positioned adjacent first and second spaced locations on the skin;
 (c) guiding a cannula through a cannula guide in the guide housing and into proximity with the blood vessel at a third location on the skin, the third location being proximate at least one of the first and second locations, or between and aligned with the first and second locations; and
 (d) inserting the cannula into the blood vessel at the third location.

25. A method as in claim 24 wherein the blood vessel is visually detectable through the skin of such patient, and including making first and second visible markings on the skin of such patient over the blood vessel at the first and second spaced locations, the marking step comprising marking the blood vessel at the first and second spaced locations through the first and second sensing guides on the guide housing when the guide housing is positioned over the blood vessel.

26. A method as in claim 24 wherein the blood vessel is visually detectable through the skin of such patient, and including making first and second visible markings on the skin of such patient over the blood vessel at the first and second spaced locations before placing the guide housing on the skin of such patient, the marking step comprising visually marking the blood vessel at the first and second locations, the spacing between the markings being estimated by the person making the markings to approximate the spacing between the sensing guides of the guide housing.

27. A method as in claim 24, the method including removing the guide housing from about the cannula through a slot in the guide housing extending through the cannula guide and one of the first and second marking guides, the cannula remaining in the blood vessel while the guide housing is removed therefrom.

28. A blood vessel cannulation device for cannulating a patient, comprising:
 (a) a mounting assembly for mounting said cannulation device proximate the skin of such patient in the vicinity of a blood vessel, said mounting assembly having a bottom;
 (b) a guide housing mounted for traverse across said mounting assembly;
 (c) a sensing guide extending through said guide housing, for inserting a sensor through said guide housing to a first end of said sensing guide proximate the skin of such patient; and
 (d) a cannula guide extending through said guide housing parallel to said sensing guide, for inserting a cannula through said guide housing to a second end of said cannula guide proximate the skin of such patient.

\* \* \* \* \*